(12) United States Patent
Smyth

(10) Patent No.: US 8,708,884 B1
(45) Date of Patent: Apr. 29, 2014

(54) SYSTEMS AND METHODS FOR ADAPTIVE MITIGATION OF MOTION SICKNESS

(71) Applicant: U.S. Army Research Laboratory, Adelphi, MD (US)

(72) Inventor: Christopher C. Smyth, Fallston, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 13/792,874

(22) Filed: Mar. 11, 2013

(51) Int. Cl.
*A61M 21/00* (2006.01)

(52) U.S. Cl.
USPC .............................................. 600/27; 706/15

(58) Field of Classification Search
USPC ...................... 600/26–28; 706/924
See application file for complete search history.

(56) References Cited

U.S. PATENT DOCUMENTS

| | | | |
|---|---|---|---|
| 4,970,683 A | 11/1990 | Harshaw et al. | |
| 5,694,939 A * | 12/1997 | Cowings | 600/484 |
| 5,829,446 A | 11/1998 | Tiffany | |
| 5,966,680 A | 10/1999 | Butnaru | |
| 6,443,913 B1 | 9/2002 | Kania | |
| 6,497,649 B2 | 12/2002 | Parker et al. | |
| 7,191,406 B1 | 3/2007 | Barber et al. | |
| 7,918,781 B1 | 4/2011 | Smyth et al. | |
| 2003/0167454 A1 | 9/2003 | Iordanov et al. | |
| 2004/0100419 A1 | 5/2004 | Kato et al. | |
| 2004/0102676 A1 | 5/2004 | Brendley et al. | |
| 2006/0079729 A1 | 4/2006 | Kim | |
| 2006/0241373 A1 | 10/2006 | Strychacz et al. | |
| 2007/0253561 A1 * | 11/2007 | Williams et al. | 381/58 |
| 2008/0270784 A1 | 10/2008 | Bonnett et al. | |
| 2009/0086021 A1 | 4/2009 | Baier et al. | |
| 2012/0075123 A1 | 3/2012 | Keinrath et al. | |

OTHER PUBLICATIONS

Gianaros PJ, Muth ER, Mordkoff JT, Levine ME, Stern RM (2001). A Questionnaire for the Assessment of the Multiple Dimensions of Motion Sickness. Aviation, Space, & Environmental Medicine, 72(2): 115-119.

Hart SG, Staveland LE (1988). "Development of NASA-TLX (Task Load Index): Results of Experimental and Theoretical Research," In P. A. Hancock & N. Meshkati (Eds.) Human Mental Workload, Amsterdam: North Holland Press.

Kennedy RS, Lane NE, Berbaum KS, Lilienthal MS (1993). "Simulator Sickness Questionnaire: An Enhanced Method for Quantifying Simulator Sickness", The International Journal of Aviation Psychology, 3(3), 203-220.

(Continued)

*Primary Examiner* — Charles A Marmor, II
*Assistant Examiner* — Carrie R Dorna
(74) *Attorney, Agent, or Firm* — Eric B. Compton

(57) ABSTRACT

Methods and apparatus for adaptively mitigating motion sickness in an operator are provided herein. In some embodiments, a compensatory modulator for use with a display controller included in a system to adaptively mitigating motion sickness in an operator may include one or more inputs to receive at least one of physiological measurements of the operator or operator activity behavior from one or more monitoring devices, and a motion sickness expert system configured to (a) determine a cognitive state of the operator based on the received inputs, (b) compute mitigating display parameters based on the determined cognitive state of the operator, (c) output the computed mitigating display parameters to the display controller.

22 Claims, 14 Drawing Sheets

(56) References Cited

OTHER PUBLICATIONS

Smyth CC (2006). Discriminant Predictors of Incapacitating Motion Sickness: A Preliminary Study, unpublished report, Army Research Laboratory, Aberdeen Proving Ground, MD 21005.

Smyth CC, Gombash JW, Burcham PM (2001). Indirect Vision Driving with Fixed Flat Panel Displays for Near-Unity, Wide, and Extended Fields of Camera View, ARL-TR-2511, Army Research Laboratory, Aberdeen Proving Ground, MD 21005.

Smyth, CC (2001). Modeling Indirect Vision Driving with Fixed Flat-panel Displays: Task Performance and Mental Workload, ARL-TR-2701, Army Research Laboratory, Aberdeen Proving Ground, MD 21005.

* cited by examiner

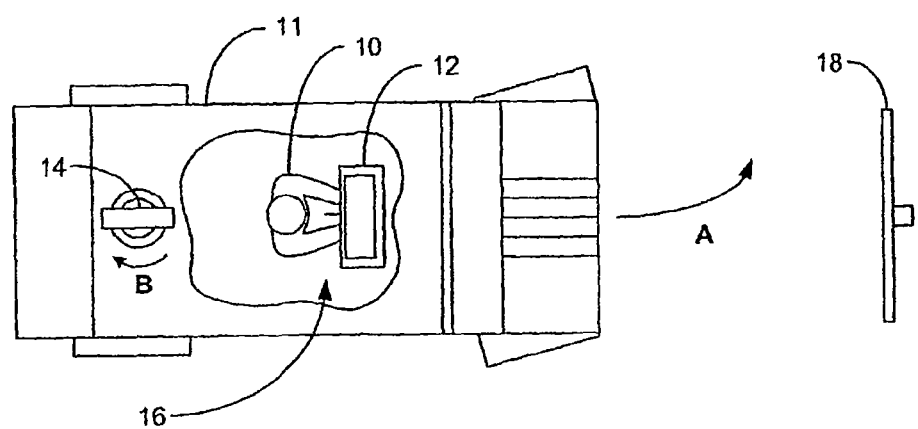
FIG. 1
(PRIOR ART)
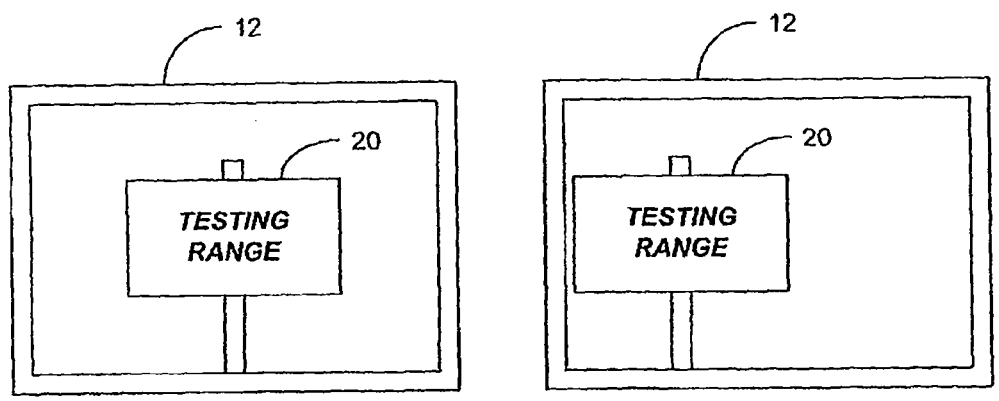
FIG. 2A
(PRIOR ART)
FIG. 2B
(PRIOR ART)

SYSTEMS AND METHODS FOR ADAPTIVE MITIGATION OF MOTION SICKNESS

GOVERNMENT INTEREST

Governmental Interest—The invention described herein may be manufactured, used and licensed by or for the U.S. Government.

FIELD

Embodiments of the present invention generally relate to the mitigation of motion sickness in human operators viewing display devices.

BACKGROUND

Motion sickness is provoked by sensory conflict between visual and sensory-motor activities that involve the vestibular system through head movements. Associated with motion sickness is a constellation of autonomic symptoms such as pallor, drowsiness, salivation, sweating, nausea and, in more severe cases, vomiting. Although some individuals eventually adapt to situations that initially provoke such sickness, others do not. In these individuals, occurrences may be severe enough to arrest task performance until the symptoms subside.

In field experiments conducted for the U.S. Army Research Laboratory on indirect-vision driving, some symptoms of motion sickness occurred in most of the participants. As shown in FIG. 1, participants, such as operator 10, drove a ground vehicle 11, while viewing a vehicle-mounted display 12. The display provided the participants with images of the external scene return from a forward-looking camera 14 mounted on the exterior of the vehicle. The cab area 16 was completely enclosed to prevent direct viewing of the external scene by the participants. On average, one out of eight participants was made sick enough to abort the driving task. Similar results have been reported for driving experiments in movement base vehicle simulators while viewing computer graphics generated terrain road scenes on a vehicle mounted display.

In another field experiment on indirect-vision driving, some participants experienced motion sickness while operating a vehicle with a vehicle mounted camera system slaved to the driver's head movement; the participants viewed the camera return through a head-mounted display and the pan and tilt motion of the camera system was computer controlled via a head tracker. The symptoms were particularly strong when operating with stereo-optics displays of slightly offset dual-camera binocular views.

In a field experiment on indirect-vision target detection from a moving vehicle with a head-mounted display, some participants experienced motion sickness while viewing the target range as the vehicle was changing course; the vehicle mounted camera system was slaved to the gunner's head movement.

In other experiments, participants have reported symptoms of motion sickness while operating a movable camera, e.g., a camera mounted on a remote vehicle, from inside a moving control vehicle. Symptoms of motion sickness can be particularly strong when the control vehicle is turning in a direction opposite to the direction of turn of the camera. In such a case, the motion of the scene viewed on the display is directly opposite to that sensed by the vestibular system of the human operator riding in the control vehicle.

With respect to the example previously provided in FIG. 1, if the vehicle 11 is turning as indicated by arrow A and the camera 14 is simultaneously rotated clockwise at a rate of turn greater than that of the vehicle (arrow B), the sequential images of the exterior scene displayed to the user are as shown in FIGS. 2A and 2B. That is, the image 20 associated with the exterior scene, e.g., the sign 18, is displayed to the operator as moving to the left across the display device 12. Since an operator is accustomed to an exterior scene moving to the right when the vehicle in which the operator is located is turning to the left, motion sickness can be induced in the operator.

Therefore, there is a need in the art for improved systems and methods to adaptively mitigate motion sickness in operators viewing display devices.

SUMMARY

Embodiments of the present invention relate to methods and apparatus for adaptively mitigating motion sickness in an operator are provided herein. In some embodiments, a compensatory modulator for use with a display controller included in a system to adaptively mitigating motion sickness in an operator may include one or more inputs to receive at least one of physiological measurements of the operator or operator activity behavior from one or more monitoring devices, and a motion sickness expert system configured to (a) determine a cognitive state of the operator based on the received inputs, (b) compute mitigating display parameters based on the determined cognitive state of the operator, and (c) output the computed mitigating display parameters to the display controller.

In some embodiments, a system for adaptively mitigating motion sickness may include a display device configured to display a first primary image and a second compensatory image, a display controller coupled to the display device and configured to control display of the second compensatory image, and a compensatory modulator communicatively coupled to the display controller, the compensatory modulator including a motion sickness expert system configured to determine a cognitive state of the operator based on at least one of physiological measurements of the operator or operator activity behavior, wherein the display controller is configured to determine display parameters of the second compensatory image based on (a) a motion of the first primary image and the display device, and (b) the determined cognitive state of the operator from the compensatory modulator.

In some embodiments, a method for adaptively suppressing motion sickness in an operator viewing a first primary image on a display device is provided and may include measuring physiological characteristics and activity behavior of the operator while viewing the first primary image, determining a cognitive state of the operator while viewing the first primary image based on the measured physiological characteristics and activity behavior, computing mitigating display parameters based on the determined cognitive state of the operator, displaying a second compensatory image on the display based on (a) a motion of the first primary image and the display device, and (b) the computed mitigating display parameters.

Other and further embodiments and variations of the invention are described in more detail, below.

BRIEF DESCRIPTION OF THE DRAWINGS

Embodiments of the present invention, briefly summarized above and discussed in greater detail below, can be understood by reference to the illustrative embodiments of the invention depicted in the appended drawings. It is to be noted, however, that the appended drawings illustrate only typical embodiments of this invention and are therefore not to be considered limiting of its scope, for the invention may admit to other equally effective embodiments.

FIG. 1 is a schematic diagram depicting a conventional vehicle in which a human operator and display device are located.

FIGS. 2A and 2B are schematic diagrams depicting conventional representative images provided by the display device of FIG. 1.

Figures 3A, 3B:
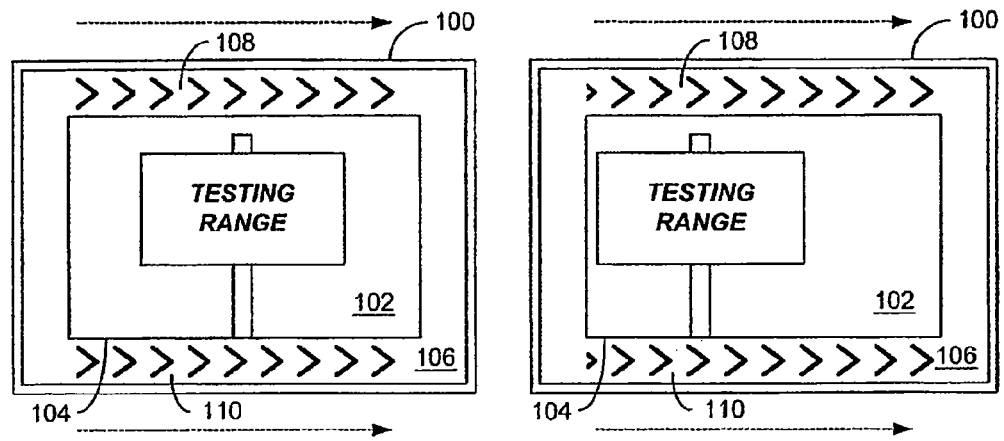
FIGS. 3A and 3B are schematic diagrams depicting images provided by a compensatory display system for suppressing motion sickness in accordance with some embodiments of the present invention.

The figures are not drawn to scale and may be simplified for clarity. It is contemplated that elements and features of one embodiment may be beneficially incorporated in other embodiments without further recitation.

DETAILED DESCRIPTION

Systems and methods are provided that can mitigate motion sickness in an operator who is viewing a scene, e.g., the scene-return from a video camera, displayed by a display device. Exemplary embodiments of a sickness suppression system may include a display device for compensating for motion sickness and a display controller of such, and a means for automatically adjusting the display to the state of the operator. The intensity of the compensatory display may be adjusted to match the motion sickness state of the viewer, increasing in intensity for mitigation as motion sickness occurs and decreasing as motion sickness is abated to decrease task interference. In this process, the optimal mitigation intensity occurs when the compensatory display appears to the user as immersed in the environment supportive of the primary task to the level of generating mitigation but not to the level of interfering. In some embodiments, this may be performed by a compensatory modulator with an embedded expert system on motion sickness. The expert system may be relatable to observables indicative of subjective feelings of motion sickness. In other embodiments, an expert system may be expanded to include the state of cognition in which self-referral induced by motion sickness, the occurrence of task immersion, and that of task interference are treated as state components. Self-referral is attention to the state of one-self as opposed to attention to the external task or the environment, in particular, to the state of the visceral senses (i.e., perception of the presence of the body's internal organs), here as induced by motion sickness. Here, task immersion occurs with senses and attention focused on the task elements when the mitigation appearing as a natural occurrence, while task distraction occurs when the mitigation appears to demand sharing of attention because of stimuli intrusion into the visual field a situation that can occur when motion sickness is not present.

First, embodiments of a compensatory display image including the compensatory display properties, and the compensatory engine used to facilitate changes the display properties in a synchronized manner so as to maintain a graded compensation in distribution and properties of the compensatory image are described below. Then, a description of at least some embodiments for the compensatory modulator and the embedded expert system on motion sickness is provided.

This application makes reference to U.S. Pat. No. 7,918, 781, naming Christopher C. Smyth et al. as inventors, and entitled: "SYSTEMS AND METHODS FOR SUPPRESSING MOTION SICKNESS", which is incorporated by reference herein.

In embodiments of the present invention, compensatory images are displayed to the operator to compensate for the displayed scene that is causing the motion sickness. The compensatory images are controlled to correspond to changes in the velocity flow of the displayed scene, as well as to accelerations sensed by the operator viewing the displayed scene. As used herein, "velocity flow" refers to the direction and speed of motion of an image with respect to the display device that is used to display the image.

With reference to FIG. 1, an operator 10 is located within a vehicle 11 in which a display device 12 is mounted. The camera 14 associated with the vehicle acquires image data corresponding to an exterior scene. In FIG. 1, the camera is acquiring images associated with a sign 18.

In the example presented with respect to FIG. 1, recall that the vehicle 11 is turning to the left (as indicated by arrow A) while the camera 14 is rotating clockwise at a rate that is greater than the turn rate of the vehicle. Therefore, the images from the camera that are displayed by the display device (FIGS. 2A and 2B) do not correspond to the sensory-motor cues sensed by the vestibular system of the operator.

FIGS. 3A and 3B schematically depict images displayed by a display device of at least one embodiment of a system for suppressing motion sickness when operating in the scenario of FIG. 1. Specifically, as shown in FIG. 3A, display device 100 includes a scene field 102 that is used for displaying images acquired by a video camera, e.g., camera 14 of FIG. 1. Outside the periphery 104 of the scene field is a compensatory field 106 that displays additional images, i.e., compensatory images. In this case, two patterns 108, 110 of compensatory images are displayed, with pattern 108 being displayed above the scene field and pattern 110 being displayed below the scene field. The compensatory images of each pattern move across the compensatory field 106 in a direction and speed that is counter to that of the images being displayed within the scene field 102. Note that in comparing FIG. 3B to FIG. 3A, the chevrons have moved to the right, with new chevrons forming at the left side of the display device. The net effect is that the combined movement of the compensatory images and the scene images displayed to the operator more closely correspond to the accelerations sensed by the operator. Although the compensatory image patterns are described herein as chevrons, other compensatory image patterns may be used, such as any morphed variations of circles which can include chevrons as an extreme, with all elements of a variation taken together forming a cloud pattern; the morphing is in the direction of flow with color for intensity.

Figure 4:
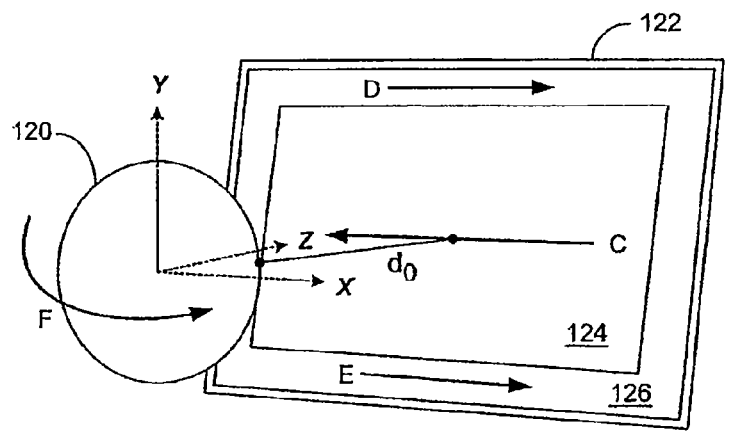
FIG. 4 is a schematic diagram of an operator viewing a display device of a system for suppressing motion sickness in accordance with some embodiments of the present invention.

FIG. 4 schematically depicts a relationship between an operator viewing an embodiment of a display device and the scene and compensatory fields of that display device. Specifically, FIG. 4 depicts an operator 120 viewing a display device 122 from a viewing distance ($d_0$). Display device 122 includes a scene field 124, which is displaying scene images that are moving to the left (indicated by arrow C), and a compensatory field 126, which is displaying compensatory images that are moving to the right (indicated by arrows D and E).

Let $V_0$ be the stable earth referenced scene velocity flow, i.e., the velocity flow of images displayed to the operator that corresponds to the motion (indicated by arrow F) sensed by the operator; let $V_S$ be the velocity flow of images displayed in the scene field 124; and let $V_C$ be the velocity flow of images displayed in the compensatory field 126. Then, $V_C = V_S - V_0$. The positive direction of the first image flow field, $V_S$, is in the opposite direction from that of the stable earth velocity and of the compensatory field; this is because the equivalent stable velocity for the first image is opposite to the velocity of the first image flow field.

The accelerations experienced by the operator are determined with respect to an arbitrary coordinate system 120 that has an x-axis parallel to the x-axis of display device 122 and a y-axis that is parallel to the y-axis of the display device. Therefore, with respect to the motion of the operator relative to the x-axis of coordinate system 120, the acceleration of the operator is expressed as $\alpha_X$. The x-axis component of the stable scene velocity flow ($V_{0X}$) is represented by $V_{0X} = (\alpha_X * d_0)^{1/2}$. Then, with $V_{SX}$ being the x-axis component for the velocity flow of images displayed in the scene field, the x-axis component of the velocity flow of images displayed in the horizontal compensatory field ($V_{CX}$) is given by $V_{CX} = V_{SX} - (\alpha_X * d_0)^{1/2}$.

Similarly, with respect to the motion of the operator relative to the y-axis of coordinate system 120, the acceleration of the operator is expressed as $\alpha_Y$. The y-axis component of the stable scene velocity flow ($V_{0Y}$) is represented by $V_{0Y} = (\alpha_Y * d_0)^{1/2}$. Then, with $V_{SY}$ being the y-axis component for velocity flow of images displayed in the scene field, the y-axis component of the velocity flow of images displayed in the (vertical side) compensatory field ($V_{CY}$) is given by $V_{CY} = V_{SY} - (\alpha_Y * d_0)^{1/2}$.

Note that, for those embodiments that consider the z-axis motion, $C_{CZ} = V_{SZ} - (\alpha_Z * d_0)^{1/2}$. By way of example, one manner to display compensatory images that vary in response to motion along the z-axis is to change the size of the compensatory images so that the images appear to get closer or move farther away from the operator. While this analysis is based on rotations, similar comments apply to linear motions.

Based on these equations, there is no velocity flow for images displayed in the compensatory field when images displayed in the scene field are moving in a direction and at a rate opposite to those of the direction and rate of the vehicle in which the operator is located. In contrast, images displayed in the scene field that are moving in the same direction as the vehicle result in an opposing velocity flow of the images displayed in the compensatory field.

In order to provide suitable compensatory images, measurements of the velocity flows of the images displayed in the scene field as well as the acceleration experienced by the operator should be real-time and accurate. In some embodiments, the velocity flow field of the images displayed in the scene field can be estimated from analysis of the images themselves. For instance, the position of a particular object displayed in the scene field can be determined periodically for measuring the velocity flow. Additionally or alternatively, information corresponding to the position, orientation and/or speed of the vehicle on which the camera that is acquiring the images for display in the scene field can be used. In the case of teleoperations, such information could be extracted from the control signals used to control the vehicle and/or camera.

The accelerations experienced by the operator can be measured by one or more sensors, e.g., accelerometers, that can be mounted in various locations. For instance, one or more sensors can be located on the display device, on the vehicle body and/or on the operator, e.g., on the operator's helmet.

Figure 5:
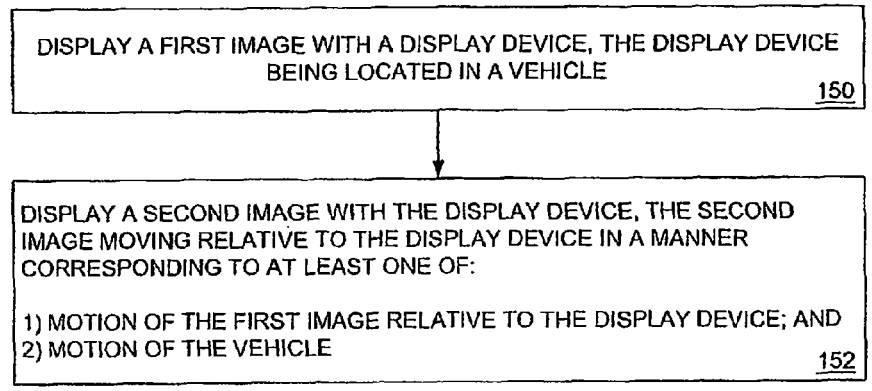
FIG. 5 is a flowchart depicting functionality of a system for suppressing motion sickness in accordance with some embodiments of the present invention.

FIG. 5 is a flowchart depicting functionality consistent with some embodiments of a system for suppressing motion sickness. As depicted in FIG. 5, the functionality (or method) may be construed as beginning at block 150, where a first image is displayed with a display device. Specifically, the display device is located in a vehicle. In block 152, a second image is displayed with the display device. In particular, the second image is displayed to move relative to the display device in a manner corresponding to at least one of: motion of the first image relative to the display device; and motion of the vehicle.

It should be noted that embodiments of the methods, apparatus and systems described herein can be implemented in software, firmware, hardware, or combinations thereof. When implemented in hardware, such a system can be implemented with any or a combination of various technologies. By way of example, the following technologies, which are each well known in the art, can be used: a discrete logic circuit(s) having logic gates for implementing logic functions upon data signals, an application specific integrated circuit(s) (ASIC) having appropriate combinational logic gates, a programmable gate array(s) (PGA), and a field programmable gate array(s) (FPGA).

When implemented in software, such a system typically is used in conjunction with a computer or processor-based device. An example computer that can be used to implement an embodiment of a system for suppressing motion sickness is depicted schematically in FIG. 6.

Figure 6:
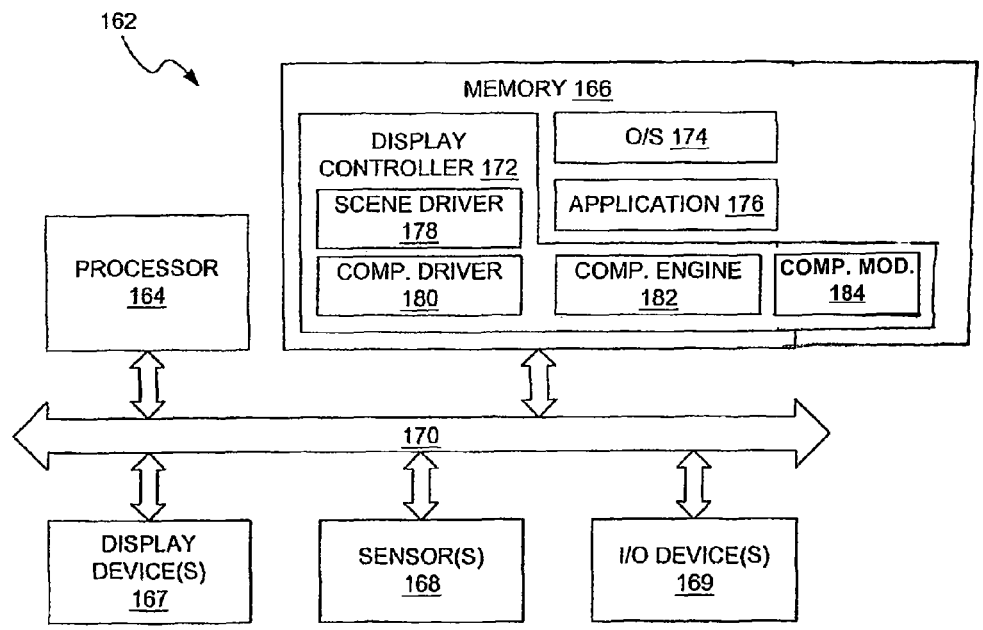
FIG. 6 is a schematic diagram of a computer or processor based device that can be used to implement a system for suppressing motion sickness in accordance with some embodiments of the present invention.

As shown in FIG. 6, embodiments of a system to adaptively mitigating motion sickness in an operator, and/or components thereof (e.g., a compensatory modulator, etc.), includes a computer 162. Computer 162 incorporates a processor 164, memory 166, a display device 167, a sensor(s) 168, and an input and/or output (I/O) device(s) 169 that are communicatively coupled via a local interface 170. The software in memory 166 can include one or more separate programs, each of which comprises an ordered listing of executable instructions for implementing logical functions. In the embodiment of FIG. 6, the software in the memory 166 includes a display controller 172, an operating system (O/S) 174, and an application 176 that provides an output to the display device. The display controller 172 includes a scene image driver 178, a compensatory image driver 180, a compensatory image engine 182, and a compensatory modulator 184.

In operation, the display controller 172 provides information to the display device 167 for displaying scene images and compensatory images. Specifically, the scene images that are displayed in the scene field of the display device are controlled by the scene image driver 178, and the compensatory images that are displayed in the compensatory field are controlled by the compensatory image driver 180. The scene image driver 178 receives information from the application 176 and/or the I/O device(s) 169 that corresponds to the scene images. The scene image driver 178, in addition to providing an input for controlling the scene field, provides an input to the compensatory image engine 182. This input is used by the compensatory image engine to determine the velocity flow of the scene images. For instance, in this embodiment, consecutive positions of a selected scene image are analyzed to determine the velocity flow. Rotational velocities of the scene images are computed from the velocity flow and the distance of the display device from the viewing position of the operator. Thus, in this embodiment, the compensatory image engine functions as an image motion sensor.

The motion of the operator is determined by the sensor(s) 168, with information from the sensor(s) being provided to the compensatory image engine. The compensatory image engine then uses the various inputs to calculate parameters associated with compensatory images that are to be displayed within the compensatory field of the display device 167. Information corresponding to the parameters of the compensatory image is provided to the compensatory image driver 180, which then provides corresponding input to the display device for controlling the compensatory images.

In some embodiments, the compensatory image engine 182 can receive an input from the application 176 that corresponds to the state of the application. For example, operator inputs to the application can be analyzed for providing predictive control to the compensatory images.

Having described compensatory displays, and the compensatory engine used to facilitate changes the compensatory image display properties, embodiments of systems and methods for suppressing motion sickness and the compensatory modulator 184 will now be described in greater detail.

Figure 7:
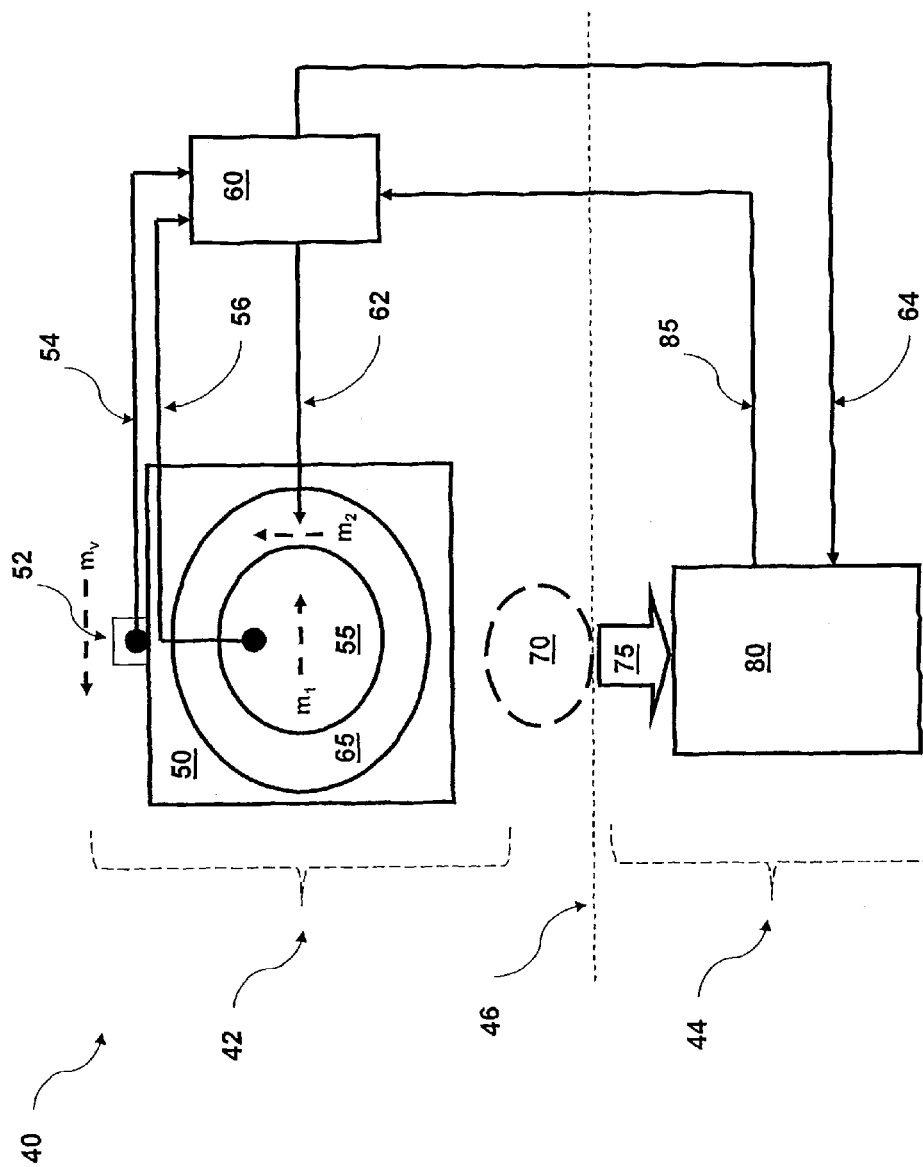
FIG. 7 is a schematic diagram of a motion sickness mitigation system in accordance with some embodiments of the present invention.

Referring to FIG. 7, a motion sickness mitigation system is depicted in accordance with some embodiments of the present invention. In some embodiments, the system 40 includes a compensatory display system 42 for suppressing motion sickness and a modulator 44 of the intensity of such a display for adaptive compensation, both systems separated 46 into two interacting components. In some embodiments, the compensatory display system consists of a display device 50 with a task display 55 and a motion sickness compensatory display 65. In some embodiments, the movement ($m_2$) of the image displayed in the compensatory display 65 may be determined by a compensatory engine 60 via control signal 62 based on the movement (m1) of the task display image (via data line 56), and the movement ($m_v$) of the display device (via data line 54) as measured by accelerometer 52, for example. The compensatory engine may determine a display format in such a manner as to maintain an inertial reference frame for the display from the accelerations and angular velocities both physical and visual sensed by the operator 70 viewing the displayed scene. Meanwhile, the compensatory modulator 80 may set the intensity (via control line 85) in accordance with the motion sickness state of the operator as determined by an embedded electronic expert system on motion sickness from activity behavior and physiological measurements 75 and display settings feedback from engine 60 (via data line 64). Here, at least one embodiment of the expert system incorporates a model of the symptomatic stages of motion sickness and in particular incapacitating motion sickness as related to the behavior and physiological measurements.

The manifestation of motion sickness has been quantified as a multidimensional construct with symptomatic components of gastrointestinal, central, peripheral, and sopite-related distresses, possibly all linked through the parasympathetic nervous system. This component of the autonomic nervous system maintains homeostasis regardless of changes in the internal being. The cumulative effect of these symptoms may be to cause an overall feeling of motion sickness. The gastrointestinal symptoms (stomach sickness, queasy, nauseated, may vomit) occur with apparent stomach discomfort. The central symptoms (faint-like, lightheaded, disoriented, dizzy, as if spinning), possibly result in a decreased capacity of the central nervous system to process task related information. In turn, the peripheral symptoms (sweaty, clammy, cold sweat, hot or warm), involve the body's peripheral response. Finally, the sopite symptoms (annoyed, irritated, drowsy, tired, fatigued, uneasy), result in disengagement from the environment possibly by sleepiness. These distinguishable symptoms that are readily observable may be differentially responsive to various types of real or apparent motion. Furthermore, individuals may experience differing degrees of activation along each of these distress dimensions in the same type of motion environment.

Subjective questionnaires have been developed by researchers for quantifying both the symptomic causes and degree of motion sickness, such as the Simulator Sickness Questionnaire (SSQ) (See Kennedy R S, Lane N E, Berbaum K S, Lilienthal M S (1993). "Simulator Sickness Questionnaire: An Enhanced Method for Quantifying Simulator Sickness", *The International Journal of Aviation Psychology*, 3(3), 203-220), based on sickness symptoms for oculomotor, disorientation, and nausea symptomatic components, and the Gianarios Motion Sickness Questionnaire (See Gianaros P J, Muth E R, Mordkoff J T, Levine M E, Stern R M (2001). "A Questionnaire for the Assessment of the Multiple Dimensions of Motion Sickness." *Aviation, Space, & Environmental Medicine,* 72(2): 115-119), based on gastrointestinal, central, peripheral, and sopite-related symptomatic components. The scoring of the degree of global motion sickness is made from a weighted summation of the subjective ratings of the component sub-scales. The ratings for the two questionnaires overlap to some degree. For example, the Gianaros Gastrointestinal measure includes distress ratings (i.e., stomach discomfort, queasy, may vomit, nauseated) that are similar to those for the SSQ Nausea measure (i.e., stomach awareness, salivation, burping, vomiting, nausea). In addition, the SSQ Nausea includes a rating (i.e., sweating) common to the Gianaros Peripheral. The Gianaros Central includes ratings (i.e., faint-like, lightheaded, disoriented, dizzy, spinning) that are similar to those of the SSQ Oculomotor (i.e., headache, difficulty focusing, eyestrain, blurred vision) and those of the SSQ Disorientation related to vestibular disturbances such as dizziness and vertigo. Similar comments apply to the scores on the Gianaros Sopite-related motion induced sub-scales of fatigue, drowsiness, and mood changes (annoyed, irritated, uneasy).

Some embodiments of the present invention use both the Gianarios Questionnaire and the SSQ frameworks. The Gianarios Questionnaire and SSQ frameworks have shown that occurrences where participants aborted an experiment (See, Smyth C C (2006). Discriminant Predictors of Incapacitating Motion Sickness: A Preliminary Study, unpublished report, Army Research Laboratory, Aberdeen Proving Ground, Md. 21005), before completion reportedly because of subjective feelings of motion sickness are highly predictable. A study of the time-history of these occurrences shows that the motion sickness builds with time to the incapacitating level. The measures of the questionnaires are linearly related at low levels of sickness intensity, but the Gianarios Gastrointestinal and SSQ Nausea measures become decoupled from the rest as the sickness intensity increases to the level of incapacitation. This parallel course with increasing sickness is to be expected since as has been mentioned, the ratings for the two questionnaires overlap to some degree, and at this higher level, the components probably correspond to the same sickness phenomena. The Gianarios Central and the Peripheral measures and the SSQ Oculomotor measure are possibly related to inducers of motion sickness that are accumulated over the experience to reach the higher-level stages of Gastrointestinal and Nausea discomfort. The measures would be decoupled since gastrointestinal distress or Nausea discomfort would be attended to at the expense of the other symptoms. The cumulative effect of these component symptoms is to cause an overall feeling of motion sickness, the occurrence of which may be severe enough to arrest task performance until the symptoms subside.

A Factor Analysis applied to the test measures, combined from both questionnaires groups the Gianarios Gastrointestinal and Peripheral measures and the Kennedy Nausea measure together separate from the rest. Using the factorial components as predictor variables in a Discriminant Analysis separates the incapacitated group from the remaining, and the drop-out points for that group from the previous ones. Similar success occurs with the sub-scales of either questionnaire as predictors as long as the Gastrointestinal or Nausea measures are included. Furthermore, the Kennedy Total Severity and Gianaros Overall summary measures being composites of the respective sub-scales separate participants who tend toward sickness from those who can be expected to complete the experiment.

Figure 8A:
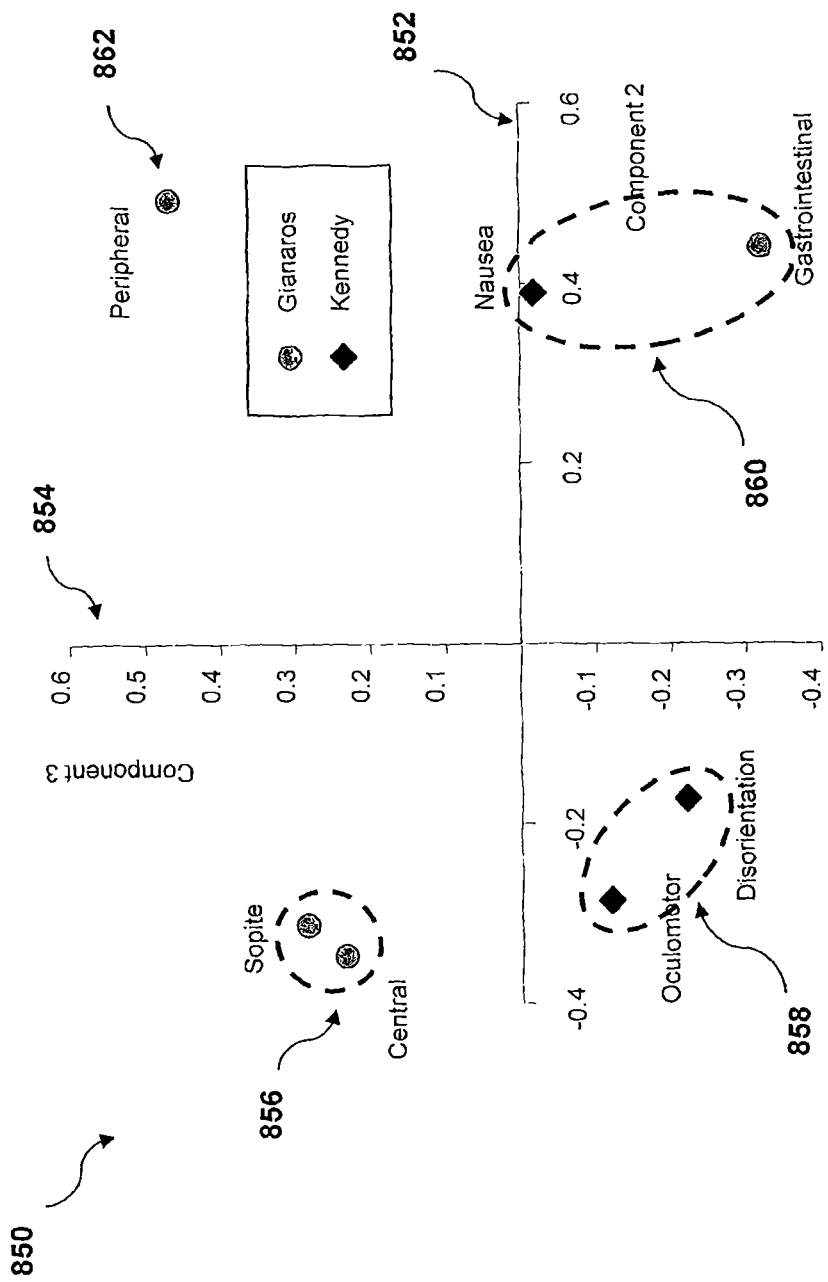
FIG. 8A is a diagram showing relationships among different motion sickness symptoms forming a basis for an expert system model in accordance with some embodiments of the present invention.

Considering the analysis results for the above mentioned research, the first factorial component separates the measures by questionnaire while the remaining two components separate measures across the questionnaires. FIG. 8A shows the factorial component loading diagram 850 for the last two components that separate measures across the questionnaires. The second component 852 groups the Nausea, Peripheral and Gastrointestinal symptomatic components together on one side of the axis and the remaining on the other. The third component 854 separates the Gastrointestinal measure and the Kennedy measures from the other Gianaros measures described above. Considering the questionnaires, the Peripheral and Gastrointestinal measures are separated from each other and from the Central and Sopite measures which are practically indistinguishable; the Nausea measure is separated from the rest of the Kennedy measures which are clustered together. The pattern is practically the same for both the measure values and the z-scores of the measures. The Central and Sopite measures are practically indistinguishable 856 and may be treated as the same measure; the same somewhat so for the Oculomotor and Disorientation 858; the Gastrointestinal and the Nausea measure may be treated together 860; these measures and the Peripheral measure 862 have practically the same loading on the 2nd component. The Gastrointestinal sub-scale measure of the Gianarios Questionnaire and the Nausea measure of the Kennedy Questionnaire are significant by the incidences of incapacitating motion sickness.

Figure 8B:
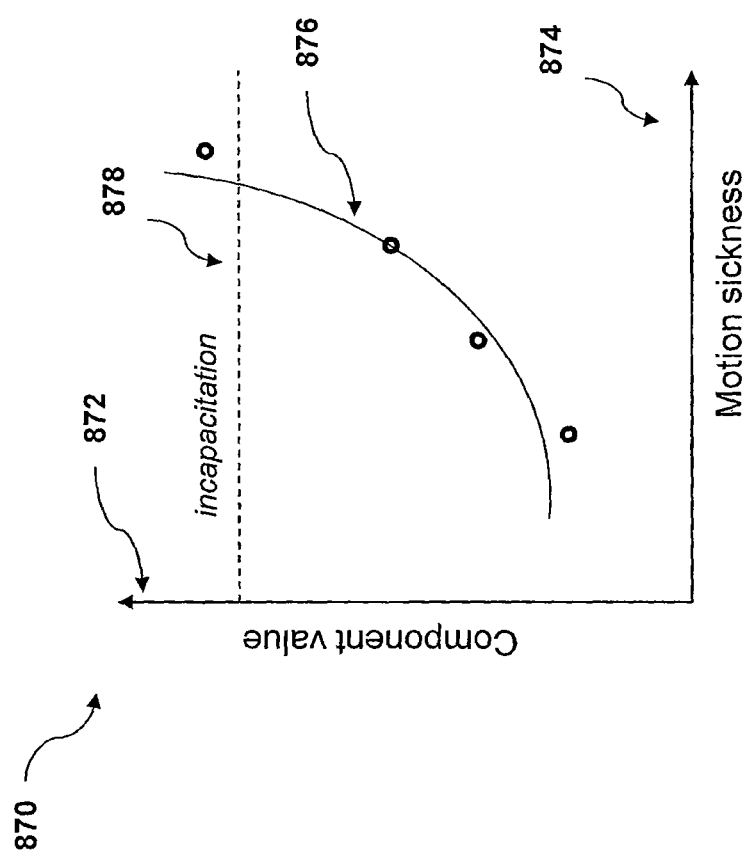
FIG. 8B is a plot of a symptom relation component versus the occurrence of motion sickness in accordance with some embodiments of the present invention.

The inventor discovered that the second factorial component separates the most significant sickness sensitive measures from the rest and that this component is significant by the trend to sickness, thus, suggesting it may be an indicator of sickness. FIG. 8B shows a plot 870 of the average value of the 2nd component 872 as a function of the sickness experience time 874 for the group that became incapacitated. The component value 872 shows a steadily increasing trend 876 with time finally reaching the value for incapacitation 878. On this basis, at least some embodiments may track motion sickness by estimating the subjective motion sickness symptoms from measurements, relating these estimates to the symptomatic component subscales, computing the resulting factorial components from the scale loadings, and using the factorial component value to estimate the degree of motion sickness.

In some embodiments, the subjective measures may be linked to physical observables of symptoms through the ratings. For example, the Gastrointestinal and Nausea symptoms of stomach discomfort and associated queasiness and feeling nauseated are symptoms of gastric distress related to a decrease in gastric motility and tonus in the muscles of the stomach that control stomach contraction. In some embodiments, this physiological activity may be measured by an electrogastrogram (EGG) from skin-surface electrodes taped onto the abdomen over the stomach region to sense the gastric myoelectric activity of the stomach muscles. In particular, an increase in gastric tachyarrhythmia, a dysrhythmic pattern of the 4 to 9 cycles per minute (CPM) gastric myoelectric activity, may be taken as a physiological indicator of the condition of gastrointestinal distress.

The Peripheral measure symptom of increased diaphorsesis or sweating (with associated feelings of clammy and a cold-sweat), is accompanied by increased skin conductivity. This physical phenomenon may be measured by a galvanic skin response using skin-surface electrodes placed, for example, on the forearm, in a bipolar configuration to measure the skin resistance to a slight current passed between the electrodes.

The Soptic measure relates to a cluster of activities made in response to motion induced excessive sensitivity with consequential avoidance of stimuli and resulting in loss of initiative and impaired cognitive concentration, that may be manifested as feelings of being annoyed, irritated, drowsy, tired, fatigued, or uneasiness, accompanied by arrested physical behavior. The arrested behavior manifested as lack of eye and body movements may be measured from scene analysis of a camera view of the user (for example, as measured by an eye-tracker, an Actimeter attached to the wrist, an electromyogram (EMG), or the like). The camera scene may show facial expressions associated with irritation and annoyance, along with activities of drooping eye lids, increased eye blinks and prolonged blinks, head in a back position or leaning forward, all associated with drowsiness. Increased brain wave spectral power in the 0.5-4.0 Hertz delta frequency band, measured by spectral analysis of electroencephalograms (EEG) are related to drowsiness.

The Central measure with feelings of faint-like, light-headed, disoriented, dizzy, spinning, and those of Disorganization (dizziness, vertigo) are related to measures of heart rate variability (increased), respiration rate (increased), and autonomic cardiac activities (decreased) of the respiratory sinus arrhythmia, all measured from analyses of the electrocardiogram (EKG). Similarly, disorientation is related to spectral power changes in the EEG, such as, for example, increased brain wave spectral power in the 0.5-4.0 Hertz delta frequency band, decreased ratio of theta wave (5-7 Hz) power to total wave (1-30 Hz) power at frontal and parietal lobes, slight increase in theta band in temporo-frontal region, and suppression of 20 and 40 Hz peaks in central posterior/occipital regions. However, changes in heart rate, respiration, and brain waves may be just as well related to task workload. The Oculomotor measures related to eye strain, difficulty focusing, blurred vision, may be measured of an analysis of facial camera scene and eye movements recorded by eye-tracker or electroculogram (EOG) showing behavior associated with attempts to re-focus.

While the above measures pertain to the state of self-referral, in some embodiments, these measures provide a framework for the cognitive state of the user as pertains to task performance on a gradient from task immersion to that of confounded. Furthermore, in embodiments consistent with the present invention, the aforementioned measures may be relatable to subjective questionnaires such as the Task Loading Index (TLX) on workload (See, Hart S G, Staveland L E (1988). "Development of NASA-TLX (Task Load Index): Results of Experimental and Theoretical Research," In P. A. Hancock & N. Meshkati (Eds.) *Human Mental Workload*, Amsterdam: North Holland Press), with ratings on symptoms of demands imposed on the user and the interaction of the user with the task. Mental, Physical, and Temporal ratings measure the demand symptoms while Effort, Frustration, and Performance ratings relate to the interaction symptoms. Factorial analysis of data results from experiments on vehicle driving with indirect vision cameras (See, Smyth C C, Gombash J W, Burcham P M (2001). *Indirect Vision Driving with Fixed Flat Panel Displays for Near-Unity, Wide, and Extended Fields of Camera View*, ARL-TR-2511, Army Research Laboratory, Aberdeen Proving Ground, Md. 21005), have shown that the workload rating measures can be factored along components of a task cognitive functional space (See, Smyth C C (2001). *Modeling indirect vision driving with fixed flat-panel displays: Task performance and mental workload*, ARL-TR-2701, Army Research Laboratory, Aberdeen Proving Ground, Md. 21005).

Again, the subjective measures are linked to physical observables of symptoms through the ratings. For example, the mental demand includes symptoms of looking and searching, which are observable from eye movement analysis, among other sources. The physical demand includes symptoms of physical activity such as pushing, pulling, turning, controlling, or activating controlling devices. A rating of the task as physically easy or demanding, slow or brisk, slack or strenuous, restful or laborious may be determined by the amount of activity. Similarly, the temporal demand includes the symptom of time pressure which may be measured from the rate or pace at which the task or task elements occur. Considering the interactive symptoms which are subjective judgments by the user, the Effort is a rating of how hard the user judges work was performed mentally and physically, Performance is a rating of the goal attainment success, while Frustration judges the degree of dissatisfaction. These ratings are again relatable to observables, particularly from the EEG.

For example, a pattern in the EEG of irregular, rapid waves with low amplitude correspond to alert, excited, and emotional states. Regular, slower, and higher amplitude waves may appear for relaxed states. Meanwhile, even larger and slower fluctuations appear when the subject is drowsy. Thus, the level of arousal from low to high can be determined from the pattern of EEG activity. In some embodiments, the member classes may include the following states: "drowsiness", "relaxed", "attentive", and "excited". The "drowsiness" state has a predominance of spectrum power in the delta band and the "relaxed" state in the alpha. The "attentive" state shows alpha suppression with strong components in the beta and gamma bands. Finally, the "excited" state has a predominance of power in the gamma band. The measured power spectrum will be distributed across these frequency bands. In turn, the logic rules judge the most preferred cognitive state to be that of attentiveness, and least those of the end extremes, drowsiness or excitement. This is based on experiments that have shown that performance is greater at the intermediate levels of arousal than at the low and high arousal states.

The physiological and eye-movement activity for task-immersion may be further described to the levels of task cognitive processing, where considering task related vision attributes, eye-blinks and eye-movement and fixation patterns may indicate the state and source of visual attention. In vehicle control with vision directed to the scene display, the visual patterns may be pursuit tracking of objects in the scene as the vehicle moves forward such as visual tracking of the road edge associated with "Skill" level driving, with occasional transient saccades to acquire new road objects that are associated with "Rules" based processing of search activity. This activity is commonly associated with a cluster of fixations once an object has been located that are used to first recognize a feature of the object for identification, and then a longer fixation for identifying the object, followed by a flurry of eye-blinks during evaluation. As has been mentioned, a shift in fixation from the scene display to the vehicle menu display may be preceded by a fixed gaze while task preparation is mentally made, presumably by priming short term memory to task schema based rules and knowledge in long term memory store. In turn, the shift may be followed by a search pattern for pertinent features of the display to complete task setup (by mapping object stimuli to schema feature framework), and finally during task execution, a disciplined pattern of fixations clustered on task pertinent features with longer fixations made in selection, and possibly eye blink flurries during a resulting manual action.

Furthermore, the general state of task attention may be determined from electrocardiogram (EKG) measurements (not shown) since the heart rate and its variability are sensitive to the cognitive workload with an increase in heart rate and a reduction in variability with increased task demands; in particular, the power spectrum of the middle frequency component (0.1 Hz) is reduced during resource limited tasks.

Still further, the state of task cognition may be determined from electroencephalogram (EEG) measurements from skin-scalp sites (not shown) of cortical brain activity; the scalp topological and power spectrum frequency distributions of the Electroencephalography (EEG), are related to cognitive processing. In particular, scalp topology spectra distributions associated with task cognitive states are:

- Task switching and recall—Strong coherence occurs in the Theta band (4-7 Hz) for the prefrontal and posterior cortical regions during task setup and recall with associated memory transfer for cognitive switching between tasks; this is followed by suppression of the upper alpha band (10-12 Hz) with memory processing at completion of task setup;
- Knowledge based reasoning—Frontal theta (4-7 Hz) activity occurs with increased mental processing during challenging tasks involving "rules" processing of knowledge; prefrontal excitation and lateralization in the anterior regions are indicative of high mental workload that is associated with "rules" and "knowledge" based reasoning;
- Rules processing—Alpha band (8-12 Hz) power decreases with task performance, at least for arithmetic, recalling, and visual and auditory memory tasks, while there is increased theta band (4-7 Hz) power during spatial and verbal tasks, with a large increase over the right hemisphere in the spatial task; and
- Repetitive skills task—A repetitive task sequence is associated with suppressed lower alpha band (8-10 Hz) involved in attention and expectancy.

Figure 9:
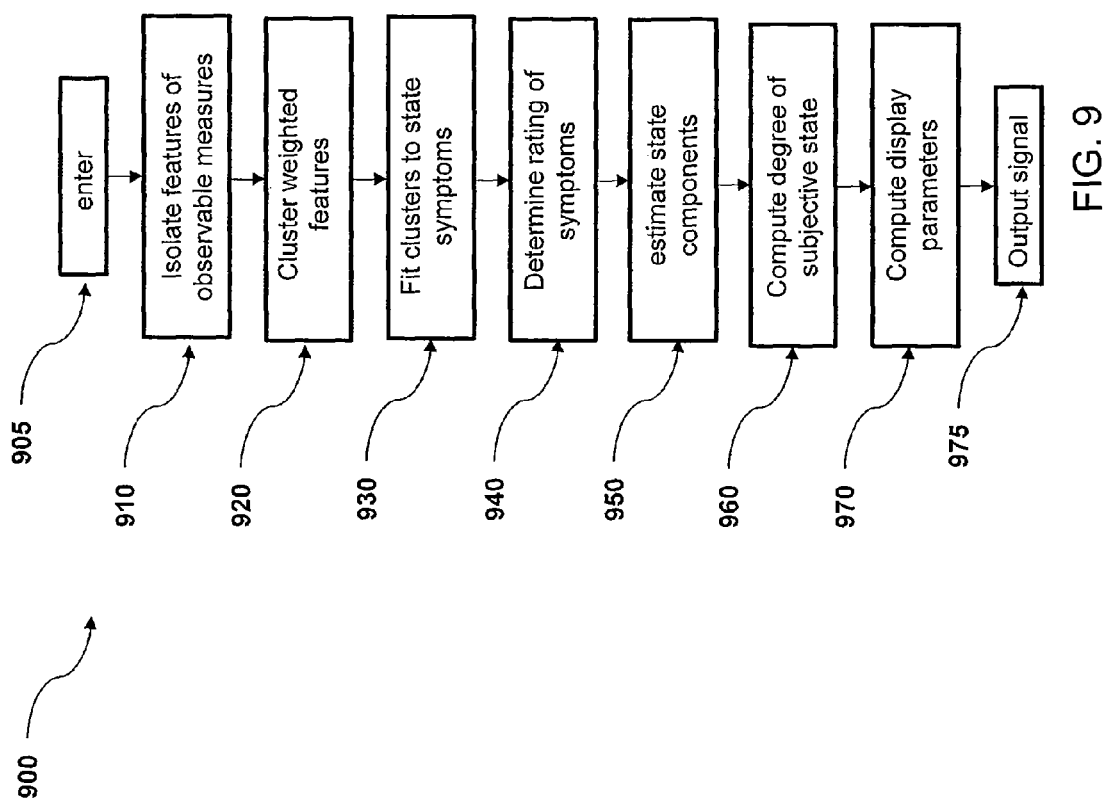
FIG. 9 is a flowchart depicting functionality of an expert system for suppressing motion sickness in accordance with some embodiments of the present invention.

In some embodiments of the present invention, the expert system estimates the cognitive state as degrees of one or more of self referral induced by motion sickness, task immersion, and task distraction by matching clusters of such measurements to a framework for equivalent subjective ratings of symptoms of the state conditions coupled to a structure incorporating a state model. Here, the subjective sub-scales are frames for the features of the observables the values of which are the scale ratings; the relations among the scalar frames construct the symptoms, and from these in turn the factorial component are computed using the factor loadings, the value of which is used to estimate the subjective degree of the cognition state. As shown in the flowchart 900 of FIG. 9, the method following program call 905, isolates pertinent features of the observable measures 910, forms clusters of weighted features 920, fits clusters to the state symptoms 930, determines the equivalent subjective ratings of the symptoms 940, estimates state components from the factorial loadings 950, computes the degree of the subjective state 960, computes the mitigating display parameters 970, and outputs the parameters to the display controller 975.

Figure 10:
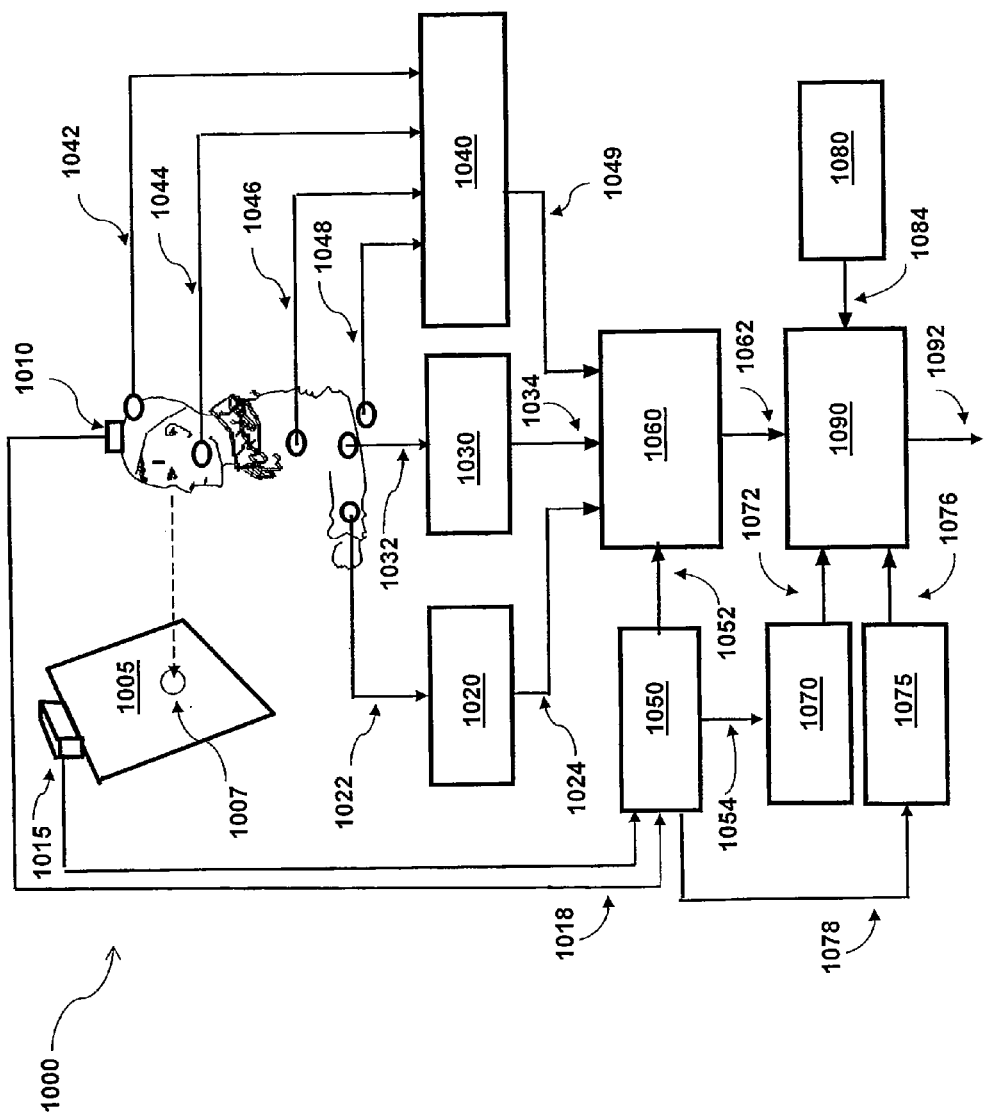
FIG. 10 is a diagram showing the elements of a compensatory display modulator for adaptive compensation by an expert system from measurements of the operator's activity and physiological state in accordance with some embodiments of the present invention.

An exemplary compensatory modulator 80 (FIG. 7), including activity behavior and physiological measurement inputs 75 consistent with at least some embodiments of the present invention is shown in FIG. 10. In some embodiments, an operator's physiological measurements are made with skin-surface electrodes for EEG 1042, EOG and EMG 1044, EKG 1046, and EGG 1048, the signals of which are processed by a physiological recorder 1040 with output 1049 to a physiological state assessor 1060. In some embodiments, the EEG recording may be made from a scalp cap of multiple electrodes judiciously distributed about the scalp (for example, in a standard 10-20 International System electrode configuration, or the like), all with amplifiers having output to the recorder 1040. In some embodiments, the EOG recordings may be made with a grid of electrodes placed above, below and laterally about the eyes with multiple amplifier outputs for measuring eye movements (vertical, lateral and blinks). In some embodiments, the EMG recordings may be made using a bipolar electrode configuration for facial and head muscles, while the EKG and EGG may employ a set of electrodes as elaborated below. Similarly, in some embodiments, the galvanic skin resistance (GSR) 1032 recording by a bipolar electrode configuration may be input to a bio-signal analyzer 1030 with output 1034 to the physiological state assessor 1060. Limb activity may be measured with an actimeter with embedded accelerometers attached to the wrist and output 1022 to motor activity estimator 1020 with output 1024 to the physiological state assessor 1060. The output 1018 of the head tracker 1010, along with the video output from the video camera 1015, goes to the eye tracker 1050 with output 1052 to the physiological state assessor 1060, output 1054 to the eye-gaze estimator 1070, and video feed-through 1078 to the facial and gesture analyzer 1075. The eye-gaze estimator 1070 outputs 1072 to a motion sickness assessor 1090 an estimate of the gaze point 1007 on the display 1005 from an embedded knowledge of the workspace geometry. With inputs 1072 from the eye-gaze estimator 1070, inputs 1062 from the physiological state assessor 1060, and 1076 from the video analyzer 1075, along with task behavior predictor 1084 from the task knowledge 1080, the motion sickness assessor 1090 outputs a control signal 1092 to the compensatory engine 60 from the embedded expert system. Here, task knowledge is embodies knowledge of the task being performed including the present state of the task and displays with feedback from the compensatory display status, and the expected manual activities and eye movements that would be made for performing the task. The task knowledge may be compared to the actual state of the task including manual and eye-movements of the operator to further determine the operator state.

Figure 11:
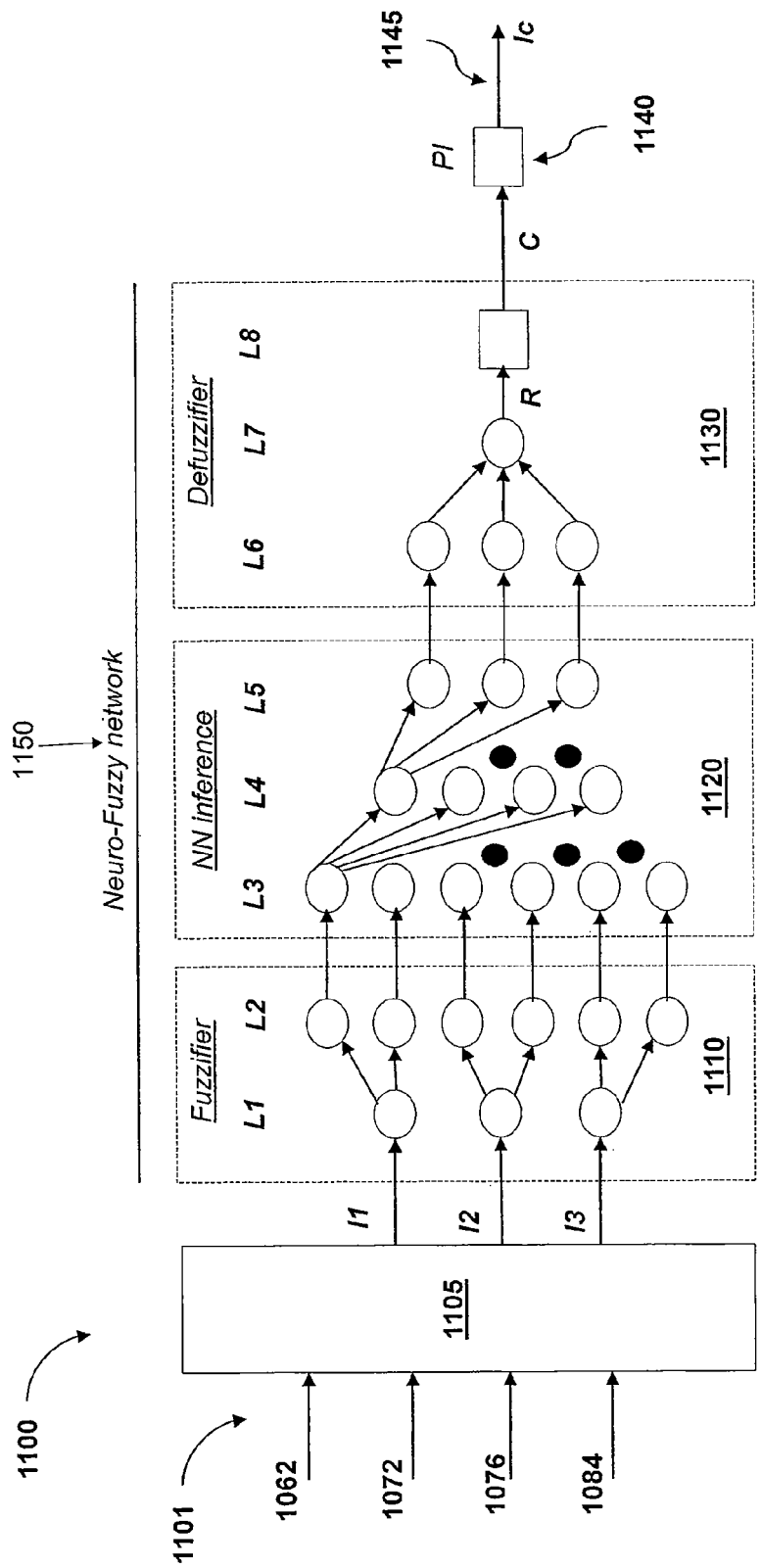
FIG. 11 is a schematic of a neuro-fuzzy logic processor for adaptive control of display parameters in accordance with some embodiments of the present invention.

At least one exemplary embodiment of the motion sickness assessor 1090 included in compensatory modulator 80 is shown in FIG. 11 as 1100. In some embodiments, the motion sickness assessor includes a cognitive state assessor 1105 with inputs 1101, in series with a neuro-fuzzy network circuit 1150. The neuro-fuzzy network circuit 1150 may consist of a fuzzifier stage 1110, a sickness inference machine 1120 (e.g., a neural network (NN) inference machine), and a defuzzifier 1130. In some embodiments, the inputs 1101 to the state assessor 1105 may consist of input 1062 from the state assessor 1060, input 1072 from eye-gaze estimator 1070, input 1076 from facial image processor 1075, and input 1084 from task behavior estimator 1080. The outputs from the state assessor 1105 to the fuzzifier 1110, consists of the degree of state estimates for self-referral (I1), task immersion (I2), and task confounded (I3). In some embodiments, the fuzzifier consists of two layers, with input layer L1 and output L2 of the linguistic level of the states. The neural network inference machine 1120, which in some embodiments may be in the form of a feed-forward propagation three layer network (input L3, output L5) with a hidden layer (L4), operates upon the input according to production rules for network connector weights between layer nodes. The production rule outputs are converted as linguistic values inputs (at layer L6) by the defuzzifier into a signal R (layer L7) and then into the rate control signal C following crisping at layer L8. The output C of defuzzifier 1130 (and neuro-fuzzy network circuit 1150) may be input to a proportional-integrator (PI) 1140 with display control signal (IC) 1145; with the integral reducing sensitivity to transients in motion sickness response.

Figure 12:
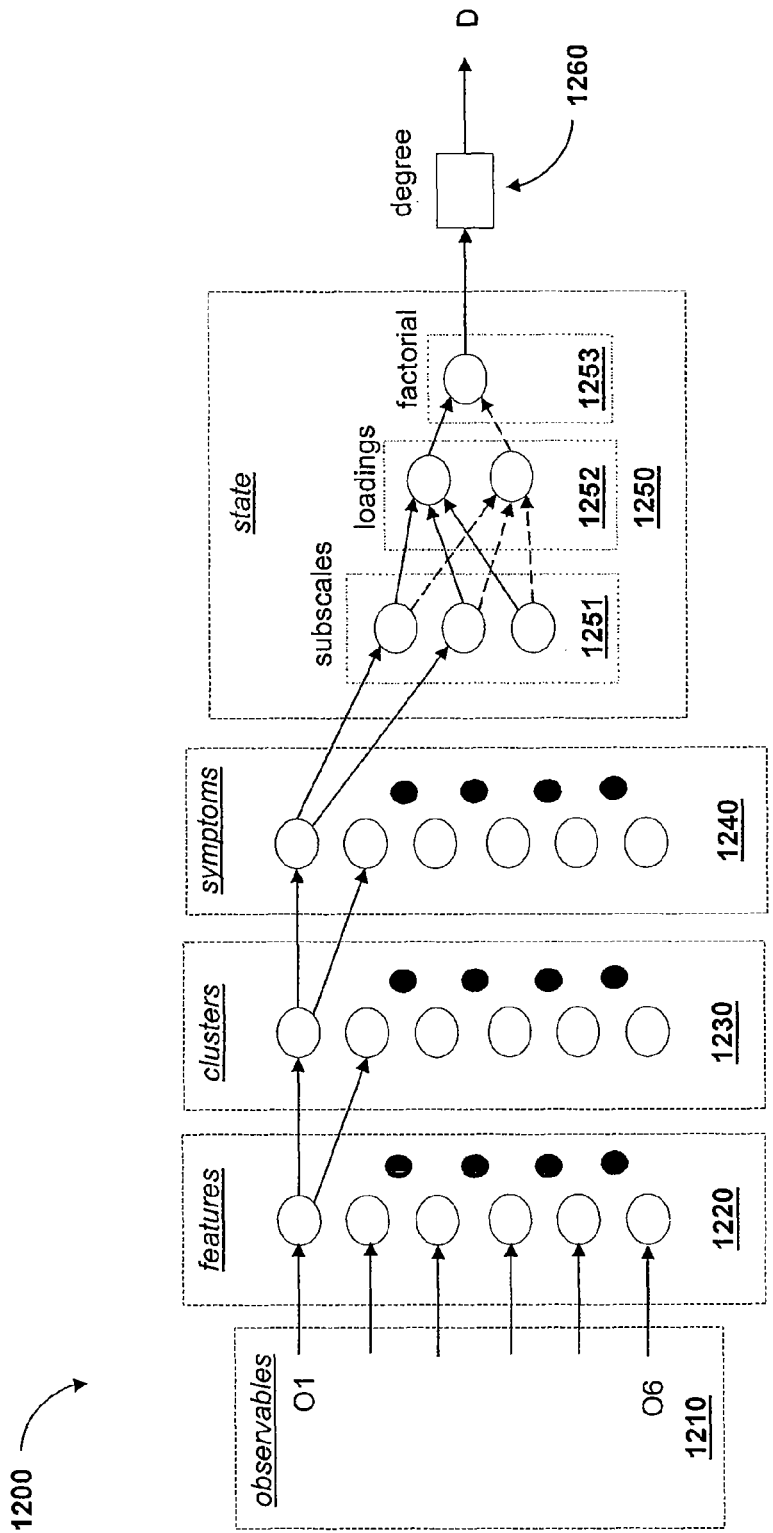
FIG. 12 is a schematic of a neural network for estimating the user-cognition state from measurements of the operator's activity and physiological state based on subjective rating relations in accordance with some embodiments of the present invention.

The state assessor 1105 may be composed of three sub processors, one for each of the states concerned, which in this embodiment, consists of state assessment for self-referral (from motion sickness), and another for the degree of task immersion and for task confounding. A state assessor subprocessor 1200 consistent with at least some embodiments of the present invention is shown in FIG. 12. In some embodiments, the state assessor sub-processor 1200 may consist of observable inputs 1210, a feature classifier 1220 for the inputs, a clustering processor 1230 with outputs to a symptoms processor 1240, and a state classifier 1250. The state classifier 1250 may further consist of a subscale rater 1251, a loading computer 1252, and computation of the factorial value 1253. In some embodiments, the factorial value 1253 is mapped to the degree of cognitive syndrome condition 1260, with degree output D as input to the fuzzifier 1110. While this may describe the state assessor for the sickness assessment, in further embodiments, a similar design is used for the task involvement states. In at least some embodiments, the feature, cluster, and symptom processors may be configured as neural networks.

Figure 13:
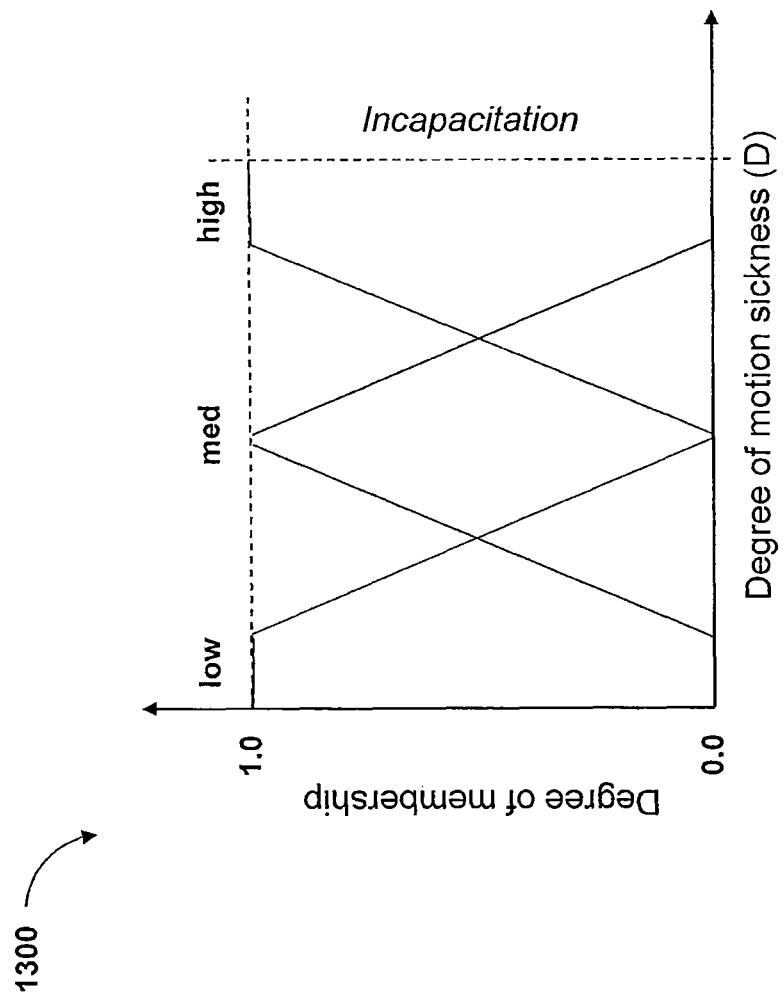
FIG. 13 is a diagram of the linguistic membership plot for the user-cognition state in accordance with some embodiments of the present invention.

In some embodiments, the fuzzifier 1110 converts the state degree to linguistic values for the membership categories 1300 as shown in FIG. 13, with standard Lambda membership functions. The degree of motion sickness is converted to membership values for the linguistic classes of 'low', 'med', and 'high' with high being bounded by the state of incapacitation. Similar linguistic values are computed for the task involvement states.

Figure 14:
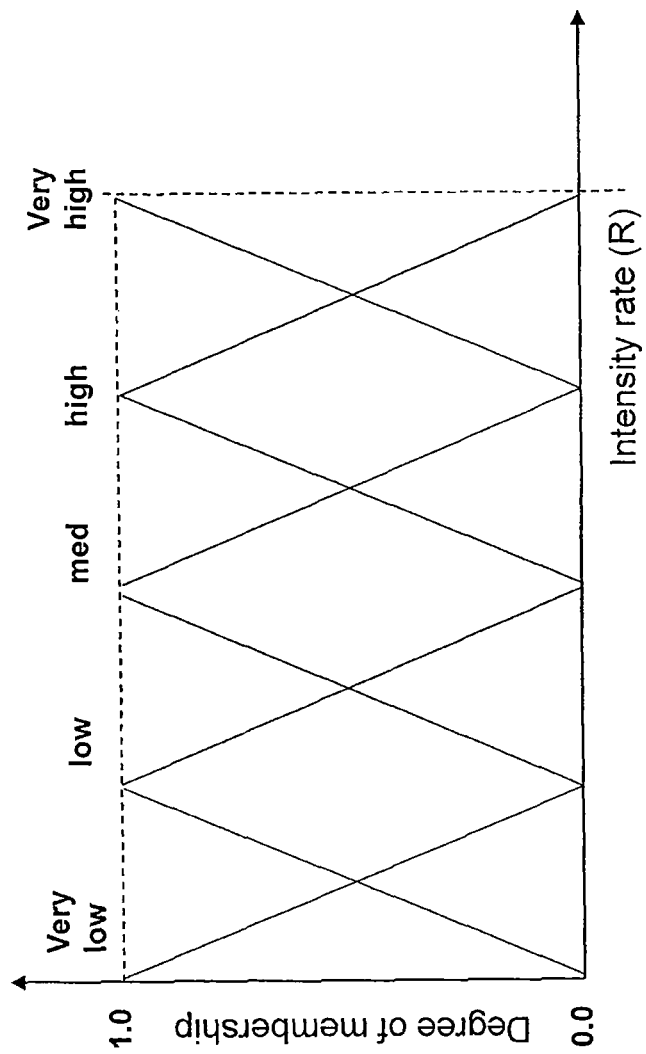
FIG. 14 is a schematic of the linguistic membership plot for the display parameter control in accordance with some embodiments of the present invention.

In further embodiments, the defuzzifier 1130 converts the linguistic values output of intensity membership from the inference rules processor 1120 according to 1400 in FIG. 14. In FIG. 14 the degrees of membership in 'very low', 'low', 'med', 'high', and 'very high' are converted to intensity rates for the classes, which are in turn converted to a single value by the crisper. In this embodiment, the 'med' degree is the null point, and the low degrees are negative rates. In some embodiments, the crisper uses a 'center-of-maximum' defuzzification method, commonly used in control applications since the method provides a continuous output, although other methods are available as well, such as the center-of gravity method, otherwise known as the 'center-of-area' method. In this method, typically, the maximum values are calculated for the membership functions of the inference rules processor, and these values are used as weights for the most typical values of the membership terms to determine the defuzzifier output of the modulator intensity rate.

In some embodiments, the inference rules processor 1120 operates according to production rules relating the state linguistic values to the intensity membership values according to the rule of Table 1. The production rules embody the knowledge of the system expressed in terms of the linguistic variables and consist of 'if condition-then action' type statements. Here, Rule 1 corresponds to the case where since the motion sickness state (MS_STATE) is 'HIGH', and the task immersion state (IM_STATE) is 'LOW', the compensatory intensity rate (RATE) is set 'VERY_HIGH'; in this rule the fuzzy logical operator .and. is the minimum of the compared values. Rule 2 corresponds to the case which since the motion sickness state is high, and the task immersion (IM_STATE) is medium ('MED'), and the task confounding (CF_STATE) is low, the rate is set low. Similarly, Rule 3 corresponds to an equilibrium point where the motion sickness is mitigated to the point where the operator can still function on the task. Rule 4 corresponds to the case where the motion sickness is low, but the compensatory display is causing task confounding. Rule 5 corresponds to the case where the motion sickness is low and the task immersion is high without a need for the compensatory display. Other rules are possible. For example, in a further embodiment, the compensatory display return 64 (FIG. 7) may be a separate output of the fuzzifier 1110 that converted to separate linguistic values may constitute a rule in the production set.

TABLE 1

| | Fuzzy Inference Production Rules |
|---|---|
| Rule 1 | if MS_STATE .eq. 'HIGH' .and. IM_STATE .eq. 'LOW' then RATE = 'VERY_HIGH' |
| Rule 2 | if MS_STATE .eq. 'HIGH' .and. IM_STATE .eq. 'MED' .and. CF_STATE .eq. 'LOW' then RATE = 'HIGH' |
| Rule 3 | if MS_STATE .eq. 'MED' .and. IM_STATE .eq. 'MED' .and. CF_STATE .eq. 'MED' then RATE = 'MED' |
| Rule 4. | if MS_STATE .eq. 'LOW' .and. IM_STATE .eq. 'MED' .and. CF_STATE .eq. 'HIGH' then RATE = 'LOW' |
| Rule 5 | if MS_STATE .eq. 'LOW' .and. IM_STATE .eq. 'HIGH' then RATE = 'VERY_LOW' |

Figure 15:
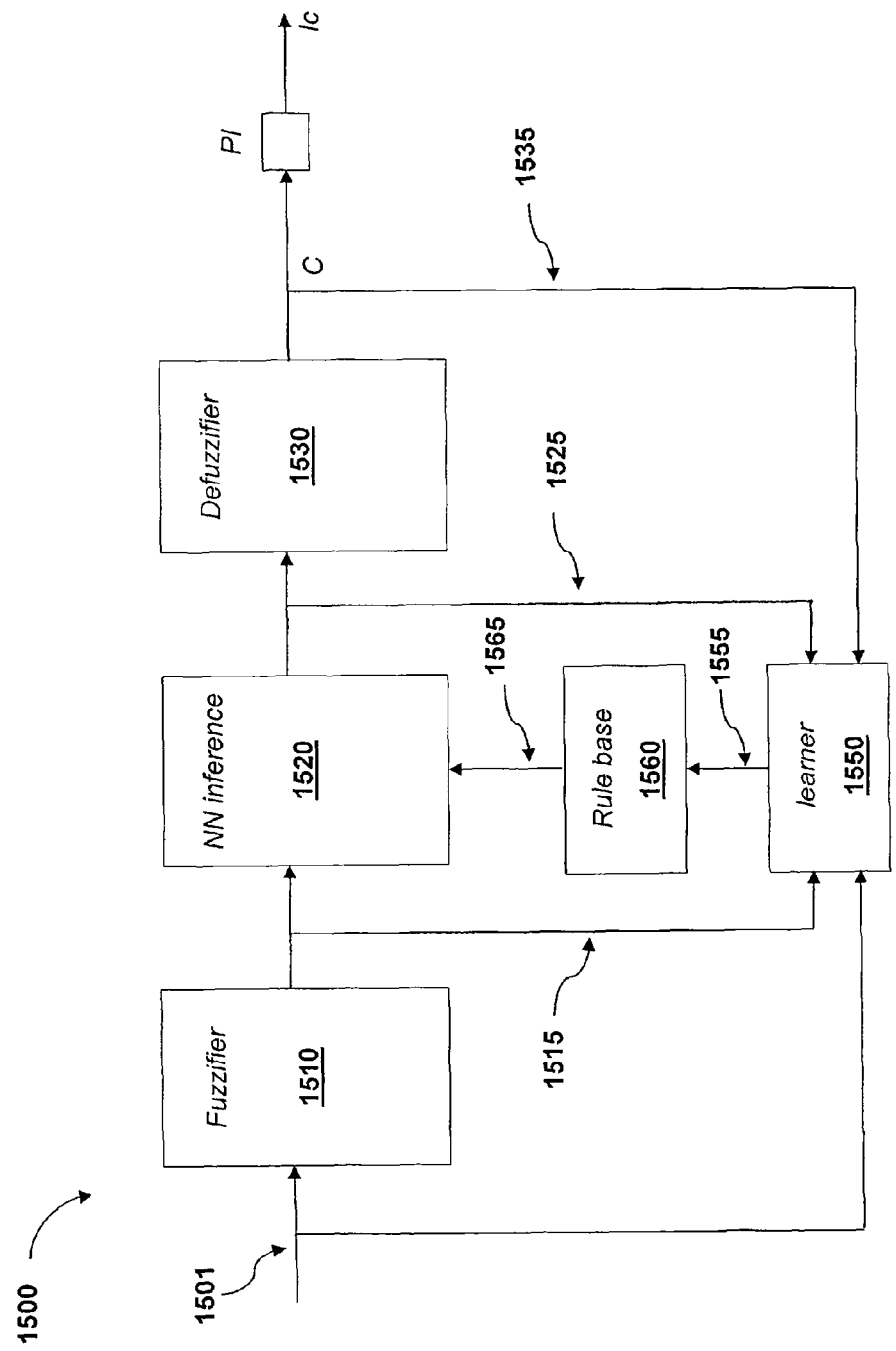
FIG. 15 is a schematic of an artificial neural network for automatic self-training of the fuzzy-logic processing rules in accordance with some embodiments of the present invention.

In other embodiments, the production rules are refined using a fuzzy logic trainer based on a neural network as shown as 1500 in FIG. 15. The input 1501 and output 1515 from the fuzzifier 1510, and the input 1525 and output 1535 from the defuzzifier 1530, are inputs to a learner 1550, with output 1555 to a rule base processor 1560. The processor outputs 1565 updates of the production rules to the inference processor 1520.

Figure 16:
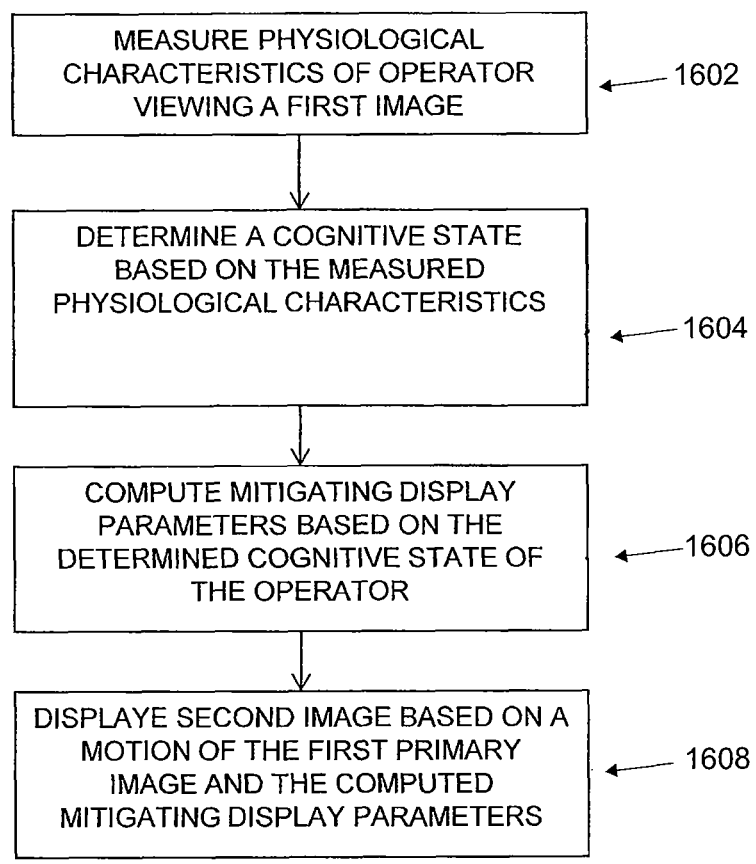
FIG. 16 depicts a flow chart of a method for adaptively suppressing motion sickness in an operator viewing a first primary image on a display device in accordance with some embodiments of the present invention.

FIG. 16 depicts a flow chart of a method 1600 for adaptively suppressing motion sickness in an operator viewing a first primary image on a display device in accordance with some embodiments of the present invention. In some embodiments, the method 1600 may be an example of a module of the memory 166 in FIG. 6 of a system for adaptively mitigating motion sickness and may be used to control the system as described herein. The method 1600 depicts a method which may be performed by system 40 of FIG. 7.

Generally method 1600 begins at 1602 where the method 1600 measures physiological characteristics and activity behavior of the operator while viewing the first primary image. At 1604, the method determines a cognitive state of the operator while viewing the first primary image based on the measured physiological characteristics and activity behavior. At 1606, mitigating display parameters are computed based on the determined cognitive state of the operator. Finally, at 1608, a second compensatory image is displayed based on the display based on (a) a motion of the first primary image and the display device, and (b) the computed mitigating display parameters.

While the foregoing is directed to embodiments of the present invention, other and further embodiments of the invention may be devised without departing from the basic scope thereof. All references mentioned herein are hereby incorporated by reference in their entireties.

The invention claimed is:

1. A compensatory modulator for use with a display controller included in a system to adaptively mitigate motion sickness of an operator in a task, the compensatory modulator comprising:
   one or more inputs to receive at least one of physiological measurements of the operator or operator activity behavior from one or more monitoring devices; and
   a cognitive state expert system configured to (a) determine whether the operator is experiencing motion sickness by determining a cognitive state of the operator based on the received inputs, (b) compute mitigating display parameters based on the determined state of the operator to mitigate determined motion sickness for that operator, and (c) output the computed mitigating display parameters to the display controller.

2. The compensatory modulator of claim 1, wherein the cognitive state expert system includes:
   a state symptomatic assessor; and
   a neuro-fuzzy network circuit communicatively coupled to the symptomatic assessor, wherein the neuro-fuzzy network circuit includes a fuzzifier module, a cognitive state inference module, and a defuzzifier module.

3. The compensatory modulator of claim 2, wherein the state inference module is a neural network inference machine.

4. The compensatory modulator of claim 2, wherein the state symptomatic assessor is configured to receive one or more inputs from at least one of an eye-gaze estimator, a facial image processor, a task activity behavior estimator, and a physiological state assessor.

5. The compensatory modulator of claim 4, wherein the physiological state assessor receives measurements of the operator from the one or more monitoring devices include at least one electroencephalogram (EEG) results, electroculogram (EOG) results, electromyogram (EMG) results, electrocardiogram (EKG) results, or electrogastrogram (EGG) results, and wherein the physiological state assessor processes the physiological measurements and sends the processed results to the cognitive state assessor inference module.

6. The compensatory modulator of claim 2, wherein the cognitive state expert system is configured to determine a cognitive state of the operator based on a symptomatic model of motion sickness as a state of self-referral and a symptomatic model of workload as a state of task involvement, at least to a level of task immersion and a level of task confounded.

7. The compensatory modulator of claim 6, wherein the symptomatic model of motion sickness is based on a rating of symptoms including at least one of gastrointestinal, central, peripheral, oculomotor, or sopite-related sickness symptoms, and wherein the symptomatic model of workload is based on a rating of symptoms for a level of task interaction and operator demand.

8. The compensatory modulator of claim 7, wherein the ratings of symptoms are determined based on clusters of observable behavior and physiological indexes, and wherein the symptoms are matched to a frame of subjective sub-scales, wherein the frame is embedded within a model of state, wherein the model of state relates the ratings of symptoms of the frame constituting subjective sub-scales to a degree of state condition.

9. The compensatory modulator of claim 2, wherein the cognitive state expert system includes a fuzzy-logic processor including a fuzzifier stage with input of the degree of state condition for states of self-referral and task involvement at least to the level of task immersion and task confounded, a cognitive state inference machine based on fuzzy production rules, and a defuzzilier stage with output of mitigating display parameters.

10. The compensatory modulator of claim 1, wherein the cognitive state expert system is further configured to: determine, based on the determined cognitive state of the operator, an intensity of the computed mitigating display parameters to be displayed.

11. The compensatory modulator of claim 10, wherein the intensity of the computed mitigating display parameters to be displayed is adjusted based on a determined motion sickness state of the operator, wherein (a) said intensity is increased as the determined motion sickness states intensifies, and (b) said intensity is decreased as the determined motion sickness of the operator abates.

12. A system for adaptively mitigating motion sickness, the system comprising:
   a display device configured to display a first primary image and a second compensatory image;
   a display controller coupled to the display device and configured to control display of the second compensatory image; and
   a compensatory modulator communicatively coupled to the display controller, the compensatory modulator including a cognitive state expert system configured to determine whether the operator is experiencing motion sickness by determining a cognitive state of the operator based on at least one of physiological measurements of the operator or operator activity behavior,
   wherein the display controller is configured to determine display parameters of the second compensatory image based on (a) a motion of the first primary image and the display device, and (b) computed mitigating display parameters based on the determined cognitive state of the operator from the compensatory modulator to mitigate determined motion sickness for that operator.

13. The system of claim 12, wherein the display controller is configured to adaptively control the display of the second compensatory image to mitigate motion sickness in a manner facilitating a cognitive state of task-immersion of the operator.

14. A method for adaptively suppressing motion sickness in an operator viewing a first primary image on a display device, the method comprising:
   measuring physiological characteristics and activity behavior of the operator while viewing the first primary image;
   determining whether the operator is experiencing motion sickness by determining a cognitive state of the operator while viewing the first primary image based on the measured physiological characteristics and activity behavior;
   computing mitigating display parameters based on the determined cognitive state of the operator to mitigate determined motion sickness for that operator; and
   displaying a second compensatory image on the display based on (a) a motion of the first primary image and the display device, and (b) the computed mitigating display parameters.

15. The method of claim 14, wherein the activity behavior is measured using at least one of an eye-gaze estimator, a facial image processor, or a task behavior estimator.

16. The method of claim 14, wherein the measured physiological characteristics include at least one electroencephalograms (EEG) results, electroculogram (EOG) results, electromyogram (EMG) results, electrocardiogram (EKG) results, or electrogastrogram (EGG) results.

17. The method of claim 14, wherein determining a cognitive state of the operator comprises determining the state as one of self-referral or of task involvement, at least to the level of task immersion or of task confounded.

18. The method of claim 17, wherein determining the state comprises clustering the physiological characteristics and activity behavior as observable features into patterns of ratings of state symptoms, computing elements of the symptom patterns as weighted by subscales, the weighted subscales as state component loadings, and the loadings as components of a factorial model of the state, where the process output is the degree of the state.

19. The method of claim 18, where the weighted subscales are equivalent to subjective subscales representative of a mental mapping of symptom patterns by the operator to the activity behavior observable features.

20. The method of claim 19, wherein the cognitive state of self-referral is determined from a symptomatic model of motion sickness, wherein the symptomatic model of motion sickness is based on at least one of gastrointestinal, central, peripheral, oculomotor, or sopite-related sickness components expressed in terms of subjective ratings of sickness symptoms, as well as a relation among the components as the motion sickness progresses to a stage of incapacitation.

21. The method of claim 19, wherein a cognitive state of task involvement is determined from a symptomatic model of workload, where the symptomatic model of workload is based on task demand and interaction components expressed in terms of subjective ratings of demand and interaction symptoms, as well as a relation among the components as the workload progresses from task immersion to task confounded.

22. The method of claim 14, wherein the method uses cognitive state linguistic membership classifications in a fuzzifier stage for degrees of self-referral and task-involvement at least to the levels of task-immersion and task-confounded, fuzzy production rules relating state memberships to display parameter linguistic membership classifications in a defuzzifier stage, with crisping for display parameter adjustments, wherein the fuzzy production rules adaptively control display parameter linguistic membership classifications so as to facilitate a cognitive state of task-immersion.

\* \* \* \* \*